(12) United States Patent
Blinka et al.

(10) Patent No.: US 6,365,245 B2
(45) Date of Patent: *Apr. 2, 2002

(54) ZEOLITE IN PACKAGING FILM

(75) Inventors: Thomas A. Blinka, Columbia, MD (US); Frank B. Edwards, Simpsonville; Nathanael R. Miranda, Spartanburg, both of SC (US); Drew V. Speer, Columbia, MD (US); Jeffrey A. Thomas, Moore, SC (US)

(73) Assignee: Cryovac, Inc., Duncan, SC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/074,058

(22) Filed: May 7, 1998

Related U.S. Application Data

(60) Division of application No. 08/812,637, filed on Mar. 7, 1997, now Pat. No. 5,834,079, which is a continuation-in-part of application No. 08/612,360, filed on Mar. 7, 1996, now abandoned.

(51) Int. Cl.⁷ .......................... B32B 27/04; B32B 27/18; G21H 5/00
(52) U.S. Cl. .............. 428/35.7; 252/181.6; 252/188.21; 252/188.28; 428/307.3; 522/79; 522/81; 522/83
(58) Field of Search .............................. 428/35.7, 35.9, 428/349, 516, 307.3; 522/83, 79, 81

(56) References Cited

U.S. PATENT DOCUMENTS 4,925,660 A * 5/1990 Atsuta et al. ................. 424/81
5,075,362 A * 12/1991 Hofeldt et al. ................. 524/72
5,126,174 A   6/1992 Courtright et al. ......... 428/34.3

(List continued on next page.)

FOREIGN PATENT DOCUMENTS

| BR | 9202713 A | 7/1992 | |
| EP | 0 638 487 A1 | 4/1994 | ........... B65D/81/34 |
| EP | WO 95/16366 | 6/1995 | |
| EP | 0 664 317 A1 | 7/1995 | |
| JP | 60163911 A * | 8/1985 | .................. 522/83 |
| JP | 05319411 A | 5/1992 | |
| JP | 05247276 | 9/1993 | |
| JP | 07227260 A | 2/1994 | |
| JP | 07227940 A | 2/1994 | |
| WO | WO 96/22160 | 7/1996 | ............ B01J/20/18 |
| WO | WO 96/40429 | 12/1996 | ............ B01J/20/18 |
| ZA | 920004298 | 4/1993 | ............ A23L/10/00 |

OTHER PUBLICATIONS

*Abscents,* Deodorizing Powder (6 pages).
*The Use of Oxygen Scavengers and Active Packaging to Reduce Oxygen Within Internal Package Environments,* Brady et al, Sep., 1995, pp. 63–67.
Molecular Sieve With Unique Structural Features Synthesized, Chemical and Engineering News, Jul. 4, 1994, p. 23.

*Primary Examiner*—Harold Pyon
*Assistant Examiner*—Sandra M. Nolan
(74) *Attorney, Agent, or Firm*—Mark B. Quatt

(57) ABSTRACT

An article of manufacture includes an oxygen scavenger and a zeolite. The article can be in the form of e.g. a film or sealing compound. A package can be made from the article for containing an oxygen-sensitive article such as food. The zeolite reduces migration of odor causing by-products of the oxygen scavenging process. A method of making an article of manufacture having reduced migration of by-products of an oxygen scavenging reaction includes providing an article including an oxygen scavenger and a zeolite; and exposing the article to actinic radiation.

7 Claims, 2 Drawing Sheets

U.S. PATENT DOCUMENTS

| | | | |
|---|---|---|---|
| 5,153,038 A | 10/1992 | Koyama et al. | 428/35.8 |
| 5,211,875 A * | 5/1993 | Speer et al. | 252/188.28 |
| 5,284,892 A | 2/1994 | Brodie, III et al. | 524/251 |
| 5,310,497 A | 5/1994 | VeSpeer et al. | 252/188.28 |
| 5,350,622 A | 9/1994 | Speer et al. | 428/215 |
| 5,362,784 A | 11/1994 | Brodie, III et al. | 524/211 |
| 5,413,827 A | 5/1995 | Brodie, III et al. | 428/35.7 |
| 5,798,055 A | 8/1998 | Blinka et al. | 252/188.28 |
| 5,993,688 A | 11/1999 | Blinka et al. | 252/188.28 |
| 6,086,786 A | 7/2000 | Blinka et al. | 252/188.28 |

* cited by examiner

ZEOLITE IN PACKAGING FILM

The present application is a divisional application of our prior U.S. patent application Ser. No. 08/812,637, filed on Mar. 7, 1997, now issued as U.S. Pat. No. 5,834,079, which is a continuation-in-part of our prior U.S. patent application Ser. No. 08/612,360 filed on Mar. 7, 1996, now abandoned, the benefit of the filing dates of which is hereby claimed under 35 U.S.C. § 120.

FIELD OF THE INVENTION

The invention generally relates to compositions, articles and methods for scavenging by-products of an oxygen scavenging reaction.

BACKGROUND OF THE INVENTION

It is well known that limiting the exposure of an oxygen-sensitive product to oxygen maintains and enhances the quality and "shelf-life" of the product. In the food packaging industry, several means for regulating oxygen exposure have already been developed.

These means include modified atmosphere packaging (MAP) for modifying the interior environment of a package; gas flushing; vacuum packaging; vacuum packaging combined with the use of oxygen barrier packaging materials; etc. Oxygen barrier films and laminates reduce or retard oxygen permeation from the outside environment into the package interior.

Another method currently being used is through "active packaging." The inclusion of oxygen scavengers within the cavity or interior of the package is one form of active packaging. Typically, such oxygen scavengers are in the form of sachets which contain a composition which scavenges the oxygen through chemical reactions. One type of sachet contains iron compositions which oxidize. Another type of sachet contains unsaturated fatty acid salts on a particulate adsorbent. Yet another type of sachet contains metal/polyamide complex.

One disadvantage of sachets is the need for additional packaging operations to add the sachet to each package. A further disadvantage arising from the use of some sachets is that certain atmospheric conditions (e.g., high humidity, low $CO_2$ level) in the package are required in order for scavenging to occur at an adequate rate.

Another means for limiting the exposure to oxygen involves incorporating an oxygen scavenger into the packaging structure itself. This achieves a more uniform scavenging effect throughout the package. This may be specially important where there is restricted air circulation inside the package. In addition, such incorporation can provide a means of intercepting and scavenging oxygen as it passes through the walls of the package (herein referred to as an "active oxygen barrier"), thereby maintaining the lowest possible oxygen level throughout the package.

One attempt to prepare an oxygen-scavenging wall involves the incorporation of inorganic powders and/or salts. However, incorporation of these powders and/or salts causes degradation of the wall's transparency and mechanical properties such as tear strength. In addition, these compounds can lead to processing difficulties, especially in the fabrication of thin films, or thin layers within a film structure. Even further, the scavenging rates for walls containing these compounds are unsuitable for some commercial oxygen-scavenging applications, e.g. such as those in which sachets are employed.

Other efforts have been directed to incorporating a metal catalyst-polyamide oxygen scavenging system into the package wall. However, this system does not exhibit oxygen scavenging at a commercially feasible rate.

Oxygen scavengers suitable for commercial use in films of the present invention are disclosed in U.S. Pat. No. 5,350,622, and a method of initiating oxygen scavenging generally is disclosed in U.S. Pat. No 5,211,875. Both applications are incorporated herein by reference in their entirety. According to U.S. Pat. No. 5,350,622, oxygen scavengers are made of an ethylenically unsaturated hydrocarbon and transition metal catalyst. The preferred ethylenically unsaturated hydrocarbon may be either substituted or unsubstituted. As defined herein, an unsubstituted ethylenically unsaturated hydrocarbon is any compound which possesses at least one aliphatic carbon-carbon double bond and comprises 100% by weight carbon and hydrogen. A substituted ethylenically unsaturated hydrocarbon is defined herein as an ethylenically unsaturated hydrocarbon which possesses at least one aliphatic carbon-carbon double bond and comprises about 50% - 99% by weight carbon and hydrogen. Preferable substituted or unsubstituted ethylenically unsaturated hydrocarbons are those having two or more ethylenically unsaturated groups per molecule. More preferably, it is a polymeric compound having three or more ethylenically unsaturated groups and a molecular weight equal to or greater than 1,000 weight average molecular weight.

Preferred examples of unsubstituted ethylenically unsaturated hydrocarbons include, but are not limited to, diene polymers such as polyisoprene, (e.g., trans-polyisoprene) and copolymers thereof, cis and trans 1,4-polybutadiene, 1,2-polybutadienes, (which are defined as those polybutadienes possessing greater than or equal to 50% 1,2 microstructure), and copolymers thereof, such as styrene-butadiene copolymer. Such hydrocarbons also include polymeric compounds such as polypentenamer, polyoctenamer, and other polymers prepared by cyclic olefin metathesis; diene oligomers such as squalene; and polymers or copolymers with unsaturation derived from dicyclopentadiene, norbornadiene, 5-ethylidene-2-norbornene, 5-vinyl-2-norbornene, 4-vinylcyclohexene, or other monomers containing more than one carbon-carbon double bond (conjugated or non-conjugated).

Preferred substituted ethylenically unsaturated hydrocarbons include, but are not limited to, those with oxygen-containing moieties, such as esters, carboxylic acids, aldehydes, ethers, ketones, alcohols, peroxides, and/or hydroperoxides. Specific examples of such hydrocarbons include, but are not limited to, condensation polymers such as polyesters derived from monomers containing carbon-carbon double bonds, and unsaturated fatty acids such as oleic, ricinoleic, dehydrated ricinoleic, and linoleic acids and derivatives thereof, e.g. esters. Such hydrocarbons also include polymers or copolymers derived from (meth)allyl (meth)acrylates. Suitable oxygen scavenging polymers can be made by trans-esterification. Such polymers are disclosed in WO 95/02616, incorporated herein by reference as if set forth in full. The composition used may also comprise a mixture of two or more of the substituted or unsubstituted ethylenically unsaturated hydrocarbons described above. While a weight average molecular weight of 1,000 or more is preferred, an ethylenically unsaturated hydrocarbon having a lower molecular weight is usable, provided it is blended with a film-forming polymer or blend of polymers.

As will also be evident, ethylenically unsaturated hydrocarbons which are appropriate for forming solid transparent layers at room temperature are preferred for scavenging oxygen in the packaging articles described above. For most applications where transparency is necessary, a layer which allows at least 50% transmission of visible light is preferred.

When making transparent oxygen-scavenging layers according to this invention, 1,2-polybutadiene is especially preferred for use at room temperature. For instance, 1,2- polybutadiene can exhibit transparency, mechanical properties and processing characteristics similar to those of polyethylene. In addition, this polymer is found to retain its transparency and mechanical integrity even after most or all of its oxygen capacity has been consumed, and even when little or no diluent resin is present. Even further, 1,2-polybutadiene exhibits a relatively high oxygen capacity and, once it has begun to scavenge, it exhibits a relatively high scavenging rate as well.

When oxygen scavenging at low temperatures is desired, 1,4-polybutadiene, and copolymers of styrene with butadiene, and styrene with isoprene are especially preferred. Such compositions are disclosed in U.S. Pat. No. 5,310,497 issued to Speer et al. on May 10, 1994 and incorporated herein by reference as if set forth in full. In many cases it may be desirable to blend the aforementioned polymers with a polymer or copolymer of ethylene.

Other oxygen scavengers which can be used in connection with this invention are disclosed in U.S. Pat. Nos. 5,075,362 (Hofeldt et al.), 5,106,886 (Hofeldt et al.), 5,204,389 (Hofeldt et al.), and 5,227,411 (Hofeldt et al.), all incorporated by reference herein in their entirety. These oxygen scavengers include ascorbates or isoascorbates or mixtures thereof with each other or with a sulfite, often sodium sulfite.

Still other oxygen scavengers which can be used in connection with this invention are disclosed in PCT patent publications WO 91/17044 (Zapata Industries) and WO94/09084 (Aquanautics Corporation), both incorporated by reference herein in their entirety. These oxygen scavengers include an ascorbate with a transition metal catalyst, the catalyst being a simple metal or salt or a compound, complex or chelate of the transition metal; or a transition metal complex or chelate of a polycarboxylic or salicylic acid or polyamine, optionally with a reducing agent such as ascorbate, where the transition metal complex or chelate acts primarily as an oxygen scavenging composition.

Yet other oxygen scavengers which can be used in connection with this invention are disclosed in PCT patent publication WO 94/12590 (Commonwealth Scientific and Industrial Research Organisation), incorporated by reference herein in its entirety. These oxygen scavengers include at least one reducible organic compound which is reduced under predetermined conditions, the reduced form of the compound being oxidizable by molecular oxygen, wherein the reduction and/or subsequent oxidation of the organic compound occurs independent of the presence of a transition metal catalyst. The reducible organic compound is preferably a quinone, a photoreducible dye, or a carbonyl compound which has absorbence in the UV spectrum.

Sulfites, alkali metal salts of sulphites, and tannins, are also contemplated as oxygen scavenging compounds.

As indicated above, the ethylenically unsaturated hydrocarbon is combined with a transition metal catalyst. While not being bound by any particular theory, the inventors observe that suitable metal catalysts are those which can readily interconvert between at least two oxidation states. See Sheldon, R. A.; Kochi, J. K.; "Metal-Catalyzed Oxidations of Organic Compounds" Academic Press, New York 1981.

Preferably, the catalyst is in the form of a transition metal salt, with the metal selected from the first, second or third transition series of the Periodic Table. Suitable metals include, but are not limited to, manganese II or III, iron II or III, cobalt II or III, nickel II or III, copper I or II, rhodium II, III or IV, and ruthenium II or III. The oxidation state of the metal when introduced is not necessarily that of the active form. The metal is preferably iron, nickel or copper, more preferably manganese and most preferably cobalt. Suitable counterions for the metal include, but are not limited to, chloride, acetate, stearate, palmitate, caprylate, linoleate, tallate, 2-ethylhexanoate, neodecanoate, oleate or naphthenate. Particularly preferable salts include cobalt (II) 2-ethylhexanoate and cobalt (II) neodecanoate. The metal salt may also be an ionomer, in which case a polymeric counterion is employed. Such ionomers are well known in the art.

The ethylenically unsaturated hydrocarbon and transition metal catalyst can be further combined with one or more polymeric diluents, such as thermoplastic polymers which are typically used to form film layers in plastic packaging articles. In the manufacture of certain packaging articles well known thermosets can also be used as the polymeric diluent.

Polymers which can be used as the diluent include, but are not limited to, polyethylene terephthalate (PET), polyethylene, low or very low density polyethylene, ultra-low density polyethylene, linear low density polyethylene, polypropylene, polyvinyl chloride, polystyrene, and ethylene copolymers such as ethylene-vinyl acetate, ethylene-alkyl (meth)acrylates, ethylene-(meth)acrylic acid and ethylene-(meth)acrylic acid ionomers. Blends of different diluents may also be used. However, as indicated above, the selection of the polymeric diluent largely depends on the article to be manufactured and the end use. Such selection factors are well known in the art.

Further additives can also be included in the composition to impart properties desired for the particular article being manufactured. Such additives include, but are not necessarily limited to, fillers, pigments, dyestuffs, antioxidants, stabilizers, processing aids, plasticizers, fire retardants, anti-fog agents, etc.

The mixing of the components listed above is preferably accomplished by melt-blending at a temperature in the range of 50° C. to 300° C. However alternatives such as the use of a solvent followed by evaporation may also be employed. The blending may immediately precede the formation of the finished article or preform or precede the formation of a feedstock or masterbatch for later use in the production of finished packaging articles.

Although these technologies offers great potential in packaging applications, it has been found that oxygen scavenging structures can sometimes generate reaction byproducts which can affect the taste and smell of the packaged material (i.e. organoleptic properties), or raise food regulatory issues. These by-products can include acids, aldehydes and ketones.

The inventors have found that this problem can be minimized by the use of zeolites (such as organophilic zeolites) which absorb odor-causing reaction byproducts. The zeolites can be incorporated into one or more layers of a multilayer film or container which includes an oxygen scavenging layer. However, one of ordinary skill in the art will readily recognize that the present invention is applicable to any oxygen scavenging system that produces by-products such as acids, aldehydes, and ketones.

DEFINITIONS

"Film" (F) herein means a film, laminate, sheet, web, coating, or the like which can be used to package a product.

"Zeolite" herein refers to molecular sieves, including aluminophosphates and aluminosilicates with a framework structure enclosing cavities occupied by large ions and/or water molecules, both of which have considerable freedom of movement permitting ion exchange and reversible dehydration. The framework may also contain other cations such as Mn, Ti, Co, and Fe. An example of such materials are the titanosilicate and titanoaluminosilicate molecular sieves. Unlike amorphous materials, these crystalline structures contain voids of discrete size. A typical naturally occurring zeolite is the mineral faujasite with formula $$Na_{13}Ca_{11}Mg_9K_2Al_{55}Si_{137}O_{384}\cdot 235H_2O.$$

Ammonium and alkylammonium cations may be incorporated in synthetic zeolites, e.g. $NH_4$, $CH_3NH_3$, $(CH_3)_2NH_2$, $(CH_3)_3NH$, and $(CH_3)_4N$. Some zeolites have frameworks of linked truncated octahedra (Beta-cages) characteristic of the structure of sodalite. Numerous synthetic zeolites are available.

"Oxygen scavenger" (OS) and the like herein means a composition, article or the like which consumes, depletes or reacts with oxygen from a given environment.

"Actinic radiation" and the like herein means any form of radiation, such as ultraviolet radiation or electron beam irradiation, disclosed in U.S. Pat. No. 5,211,875 (Speer et al.).

"Polymer" and the like herein means a homopolymer, but also copolymers thereof, including bispolymers, terpolymers, etc.

"Ethylene alpha-olefin copolymer" and the like herein means such heterogeneous materials as linear low density polyethylene (LLDPE), linear medium density polyethylene (LMDPE) and very low and ultra low density polyethylene (VLDPE and ULDPE); and homogeneous polymers such as metallocene catalyzed polymers such as EXACT (™) materials supplied by Exxon, and TAFMER (™) materials supplied by Mitsui Petrochemical Corporation. These materials generally include copolymers of ethylene with one or more comonomers selected from $C_4$ to $C_{10}$ alpha-olefins such as butene-1 (i.e., 1-butene), hexene-1, octene-1, etc. in which the molecules of the copolymers comprise long chains with relatively few side chain branches or cross-linked structures. This molecular structure is to be contrasted with conventional low or medium density polyethylenes which are more highly branched than their respective counterparts. Other ethylene/alpha-olefin copolymers, such as the long chain branched homogeneous ethylene/alpha-olefin copolymers available from the Dow Chemical Company, known as AFFINITY (™) resins, are also included as another type of ethylene alpha-olefin copolymer useful in the present invention.

As used herein, the term "polyamide" refers to polymers having amide linkages along the molecular chain, and preferably to synthetic polyamides such as nylons. Furthermore, such term encompasses both polymers comprising repeating units derived from monomers, such as caprolactam, which polymerize to form a polyamide, as well as copolymers of two or more amide monomers, including nylon terpolymers, also referred to generally as "copolyamides" herein.

"LLDPE" herein means linear low density polyethylene, which is an ethylene alpha olefin copolymer.

"EVOH" herein means ethylene vinyl alcohol copolymer.
"EVA" herein means ethylene vinyl acetate copolymer.

SUMMARY OF THE INVENTION

In one aspect of the invention, an article of manufacture comprises an oxygen scavenger and a zeolite.

In a second aspect of the invention, a package comprises an article and a container into which the oxygen sensitive article is disposed, the container including a component comprising an oxygen scavenger and a zeolite.

In a third aspect of the invention, a method of making an article of manufacture having reduced migration of by-products of an oxygen scavenging reaction comprises providing an article comprising an oxygen scavenger and a zeolite and exposing the article to actinic radiation.

BRIEF DESCRIPTION OF THE DRAWINGS

The invention may be further understood with reference to the drawings wherein.

DESCRIPTION OF THE PREFERRED EMBODIMENTS

The invention can be used to make various articles of manufacture, compositions of matter, coatings, etc. Two preferred forms are sealing compositions, and flexible films, both useful in packaging of food and non-food products.

It is known to use sealing compositions in the manufacture of gaskets for the rigid container market. Large, wide diameter gaskets are typically made using a liquid plastisol. This plastisol is a highly viscous, liquid suspension of polymer particles in a plasticizer. In the manufacture of metal or plastic caps, lids, and the like, this liquid plastisol is applied to the annulus of a container such as a jar, and the container with the applied plastisol is "fluxed" in an oven to solidify the plastisol into a gasket. The result is a gasket formed around the annulus of the container.

Smaller gaskets are typically made for use in beer crowns in bottles. A polymer melt is applied by cold molding to the entire inner surface of the crown. Both PVC and other polymers are used in this application.

Discs for plastic caps are typically made by taking a ribbon of gasket material and making discs, and inserting the discs into the plastic cap.

In all of these applications, the use of an oxygen scavenger and zeolite beneficially provides removal of oxygen from the interior environment of the container, while controlling undesirable by-products of the oxygen scavenging reaction.

Thus, a gasket includes a polymeric composition, an oxygen scavenger, and a zeolite. The gasket adheres a metal or plastic lid or closure to a rigid or semi-rigid container, thus sealing the lid or closure to the container.

Figure 1:
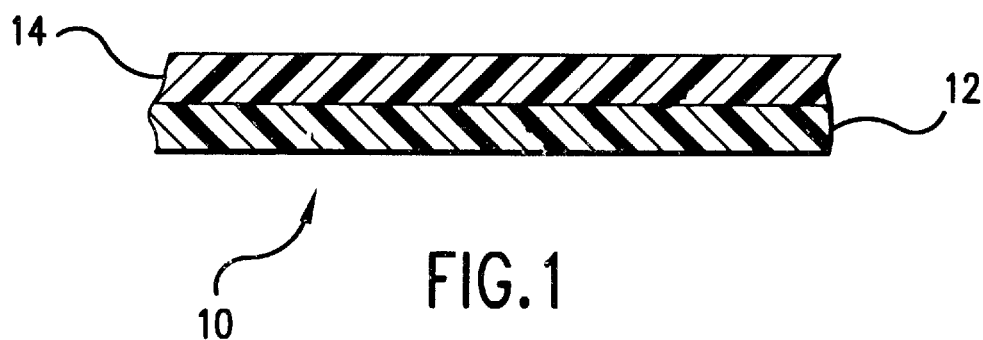
FIGS. 1 through 5 are schematic cross-sections of various embodiments of a film of the present invention.

Referring to FIG. 1, a multilayer film 10 is shown, having layer 12 and layer 14.

Figure 2:
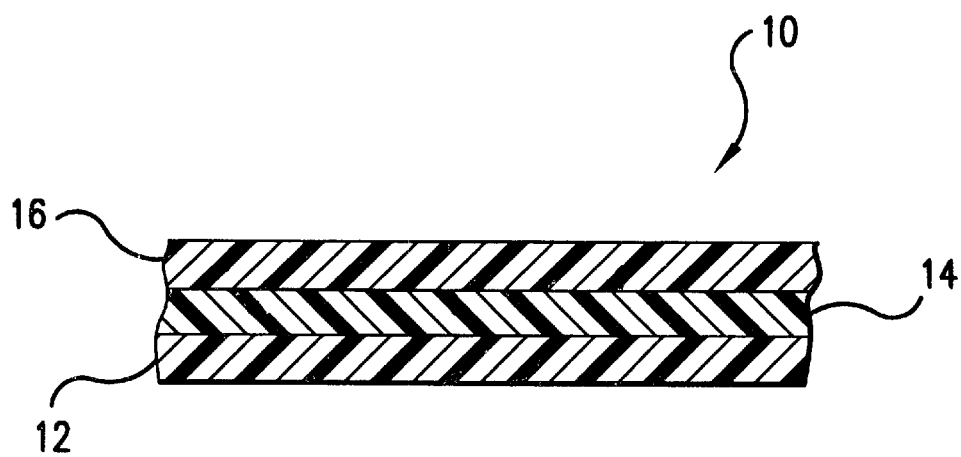

FIG. 2 shows a multilayer film with layers 12, 14, and 16. Layers 12, 14, and 16 are preferably polymeric.

Layer 12 comprises a zeolite. Preferred materials are the molecular sieves of the type disclosed in U.S. Pat. No. 4,795,482 (Gioffre et al.), incorporated herein by reference in its entirety. Also useful in the present invention are zeolites supplied by the Davison division of W. R. Grace & Co.-Conn. Preferred particle sizes for zeolites used in the present invention are between 0.1 and 10 micrometers, and more preferably between 0.5 and 3 micrometers.

Layer 14 comprises an oxygen scavenger, preferably a polymeric oxygen scavenger, more preferably one of the materials described above.

Layer 16 comprises an oxygen barrier material, such as ethylene vinyl alcohol copolymer (EVOH), Saran (vinylidene chloride copolymer), polyester, polyamide, metal, silica coating, etc.

Figure 3:

FIG. 3 shows a laminated film in which a three layer film is adhered to a second film. Layers 32, 34, and 36 correspond functionally and compositionally to 12, 14, and 16 respectively of FIG. 2, and layer 38 is an intermediate layer which can comprise any polymeric material such as polyolefin, more preferably ethylenic polymers such as ethylene/alpha-olefin and ethylene/unsaturated ester copolymers, more preferably ethylene/vinyl acetate copolymer. Layer 31 represents a conventional adhesive such as polyurethane adhesive. Comparative 2 in Table 6 exemplifies the laminated film of FIG. 3.

Figure 4:
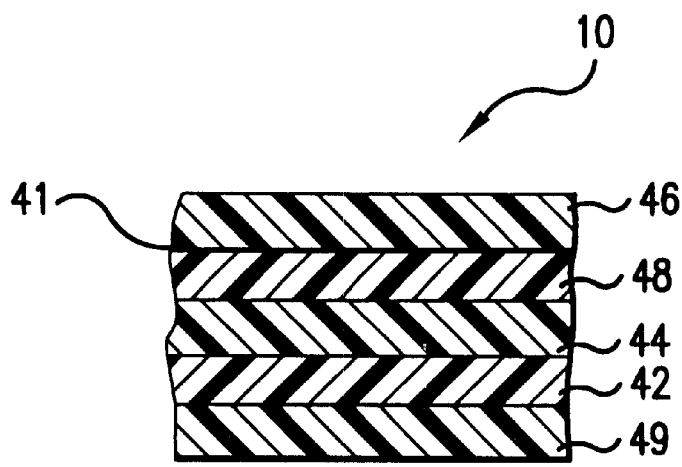

FIG. 4 shows a laminated film in which a four layer film is adhered to a second film. Layers 42, 44, 46 and 48 correspond functionally and compositionally to layers 32, 34, 36 and 38 respectively of FIG. 3. Layer 49 is an innermost heat sealable layer which can comprise any polymeric material such as polyolefin, more preferably ethylenic polymers such as ethylene/alpha-olefin and ethyene/unsaturated ester copolymers, such as ethylene vinyl acetate copolymer. Layer 46 provides oxygen barrier to the film structure, and adheres to layer 48 by means of conventional adhesive 41. This adhesive corresponds to layer 31 of FIG. 3, and is shown simply as a thickened line. Examples 2 and 3 of Table 6 exemplify the laminated film of FIG. 4.

Figure 5:
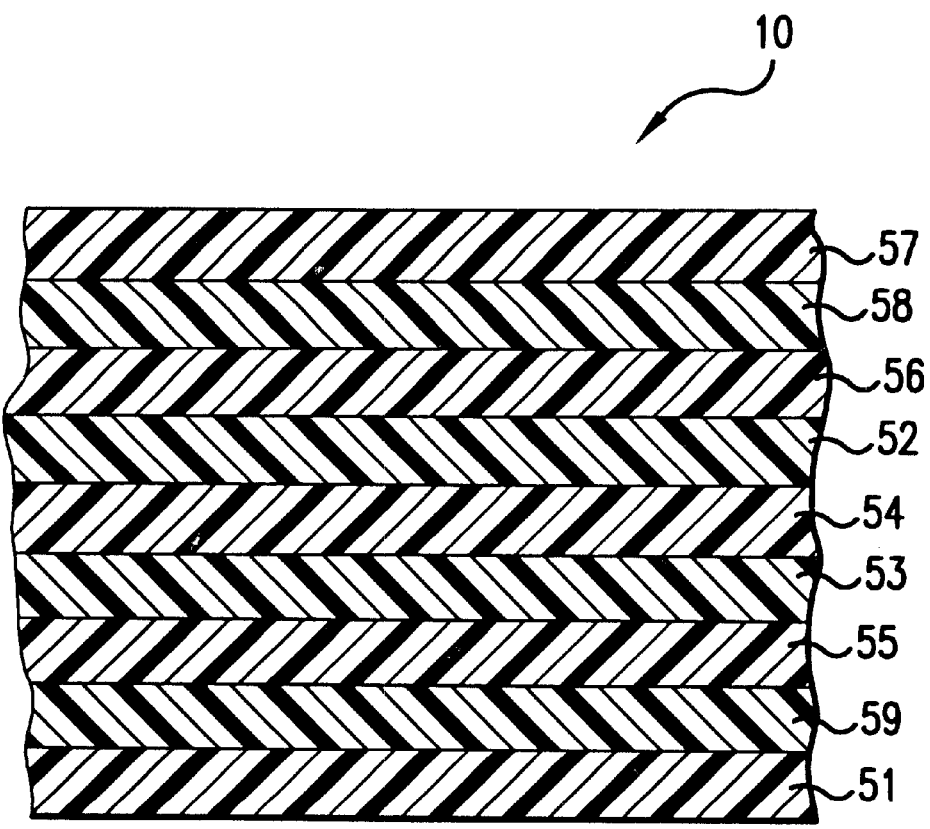

FIG. 5 shows a nine layer film. Example 1 and Comparative 1 in Table 2 exemplify the film of FIG. 5.

Layer 57 is an abuse-resistant layer useful as an outermost layer of a film when used in a packaging application.

Layers 54 and 56 correspond functionally and compositionally to layers 14 and 16 respectively of FIGS. 2 and 3, as well as to layers 44 and 46 respectively of FIG. 4.

Layers 52, 53, 58 and 59 comprise an adhesive. The adhesive is preferably polymeric, more preferably acid or acid anhydride-grafted polyolefins. In addition, these layers can comprise a zeolite.

Layer 55 comprises a heat resistant material. This can be any suitable polymeric material, preferably an amide polymer such as nylon 6, or a polyester such as polyethylene terephthalate.

Layer 51 comprises a heat sealable material. This can be any suitable polymeric material, preferably an olefinic polymer such as an ethylenic polymer, more preferably an ethylene alpha olefin copolymer. In addition, layer 51 can further comprise a zeolite.

The invention may be further understood by reference to the examples shown below. Table 1 identifies the materials used in the examples. The remaining tables describe the films made with these materials, and organoleptic or migration data resulting from testing some of these films.

TABLE 1

| MATERIAL | TRADENAME | SOURCE | DESCRIPTION |
|---|---|---|---|
| $PE_1$ | Dowlex ™ 3010 | Dow | LLDPE, an ethylene/1-octene copolymer with a density of 0.921 gm/cc |
| $PE_2$ | Dowlex ™ 2244 A | Dow | LLDPE, an ethylene/1-octene copolymer with a density of 0.916 gm/cc |
| $PE_3$ | Poly-eth 1017 | Chevron | low density polyethylene |
| $PE_4$ | AC-9A | Allied | polyethylene powder |
| $AB_1$ | 10,075 ACP Syloid ™ antiblock concentrate | Tecknor Color | 89.8% low density polyethylene (Exxon LD 203.48) + 10% synthetic amorphous silica (Syloid ™ 74X6500 from Davison Chemical) + 0.2% calcium stearate |
| $PP_1$ | Escorene PP292.E1 | Exxon | polypropylene |
| $Z_1$ | 10414-12 zeolite concentrate | Colortech | masterbatch of 80% LLDPE and 20% UOP Abscents ® 3000 zeolite |
| $Z_2$ | 10417-12 zeolite concentrate | Colortech | masterbatch of 80% LLDPE and 20% UOP Abscents ® 2000 zeolite |
| $Z_3$ | USY zeolite | Grace Davison | zeolite |
| $Z_4$ | ZSM-5 zeolite | Grace Davison | zeolite |
| $Z_5$ | ZN-1 | Grace Davison | zeolite |
| $Z_6$ | X5297H | Engelhard | titanium silicate zeolite |
| $AD_1$ | Plexar ™ 107 | Quantum | anhydride-grafted EVA |

TABLE 1-continued

| MATERIAL | TRADENAME | SOURCE | DESCRIPTION |
|---|---|---|---|
| $AD_2$ | Adcote 530 and Coreactant 9L23 | Morton International | mixture of silane, isocyanate, glycol, and alkyl acetate |
| $PA_1$ | Ultramid ™ KR 4407-F | BASF | nylon 6 (polycaprolactam) |
| $OB_1$ | LC-H101BD | Evalca | ethylene/vinyl alcohol copolymer with 38 mole % ethylene |
| $OS_1$ | RB-830 | JSR | 1,2-polybutadiene |
| $OS_2$ | VISTALON ™ 3708 | Exxon | ethylene-propylene-diene terpolymer |
| $OS_3$ | VECTOR ™ 8508-D | Dexco | styrene/butadiene copolymer with 30% by weight of the styrene comonomer, and 70% by weight of the butadiene comonomer |
| $EV_1$ | MU-763 | Quantum | ethylene/vinyl acetate copolymer |
| $EV_2$ | PE 1375 | Rexene | ethylene/vinyl acetate copolymer with 3.6 wt. % vinyl acetate comonomer |
| $EV_3$ | LD-318.92 | Exxon | ethylene/vinyl acetate copolymer with 9 wt. % vinyl acetate comonomer |
| $EB_1$ | Lotryl 30BA02 | Atochem | ethylene/butyl acrylate copolymer with 30 wt. % butyl acrylate copolymer |
| $PI_1$ | benzophenone | Sartomer | photoinitiator |
| $PI_2$ | benzoylbiphenyl | — | photoinitiator |
| $TC_1$ | TENCEM ™ 170 | OMG | cobalt neodecanoate, a transition metal catalyst |
| $TC_2$ | cobalt oleate | Shepherd | a transition metal catalyst |
| $F_1$ | 50m-44 Mylar ™ | DuPont | Saran-coated polyethylene terephthalate film |

Certain materials were blended together for some of the film structures, and these blends are identified as follows:

$PEB_1 = 90\% \ PE_1 + 10\% \ AB_1$.

$PEB_2 = 90\% \ PE_1 + 10\% \ PEB_3$.

$PEB_3 = 80\% \ PE_3 + 20\% \ PE_4$.

$PPB_1 = 60\% \ PP_1 + 40\% \ EB_1$.

$PPB_2 = 40\% \ PP_1 + 60\% \ EB_1$.

$OSB_1 = 76.5\% \ OS_1 + 13.5\% \ OS_2 + 9.2\% \ EV_1 + 0.5\% \ PI_1 + 0.3\% \ TC_1$.

$OSB_2 = 50\% \ OS_3 + 40\% \ PE_3 + 8.54\% \ EV_1 + 0.90\% \ TC_1 + 0.50\% \ PI_1 + 0.05\%$ calcium oxide+0.01% antioxidant (Irganox 1076).

$OSB_3 = 60\% \ OS_3 + 38.83\% \ EV_3 + 1.06\% \ TC_2 + 0.10\% \ PI_2 + 0.01\%$ antioxidant (Irganox 1076).

$OSB_4 = 40\% \ OS_3 + 58.83\% \ EV_3 + 1.06\% \ TC_2 + 0.10\% \ PI_2 + 0.01\%$ antioxidant (Irganox 1076).

$ZB_1 = 87\% \ PE_1 + 10\% \ AB_1 + 3\% \ Z_1$.

$ZB_2 = 90\% \ PE_2 + 10\% \ Z_1$.

$ZB_3 = 90\% \ PE_2 + 10\% \ Z_2$.

$ZB_4 = 90\% \ PE_2 + 6\% \ PE_3 + 2\% \ PE_4 + 1\% \ Z_3 + 1\% \ Z_4$ $ZB_5 = 80\% \ PE_2 + 20\% \ Z_2$.

$ZB_6 = 80\% \ PE_3 + 20\% \ Z_2$.

In Table 2, a nine-layer film structure in accordance with the invention, and a comparative film, are disclosed. These were each made by coextrusion of the layers.

TABLE 2

| EXAMPLE | STRUCTURE |
|---|---|
| 1 | $PEB_1/AD_4/OB_1/AD_4/OSB_1/AD_4/PA_1/AD_4/ZB_2$ |
| COMP. 1 | $PEB_1/AD_4/OB_1/AD_4/OSB_1/AD_4/PA_1/AD_4/PEB_1$ |

The target (and approximate actual) gauge (in mils) of each layer of the nine-layer film is shown below. Layer 9 would preferably form the food or product contact layer in a typical packaging application.

| layer 1 | layer 2 | layer 3 | layer 4 | layer 5 | layer 6 | layer 7 | layer 8 | layer 9 |
|---|---|---|---|---|---|---|---|---|
| 1.35 | 0.20 | 0.50 | 0.20 | 0.50 | 0.20 | 1.00 | 0.20 | 1.35 |

The films of Example 1 and Comparative 1 were subjected to food law migration tests to evaluate whether zeolites could reduce the concentration of extractables. The films were triggered by ultraviolet light according to the procedure disclosed in U.S. Pat. No. 5,211,875. The films were converted into 280 cm² pouches and the pouches were filled with a food simulant. The filled pouches were then retorted at 100° C. for 30 minutes and stored at 50° C. for 10 days. The food simulant was decanted from the pouches and analyzed. Table 3 shows a list of potential extractables. Table 4 shows the concentration of the same extractables, where the films were extracted with 8% ethanol solution as the food simulant. Table 5 shows the concentration of the same extractables, where the films were extracted with water as the food simulant. In both Tables 4 and 5, the concentration of each extractable is in units of nanograms/milliliter. Zeolites can reduce the concentration of certain extractables which could cause regulatory issues.

TABLE 3

| ABBREVIATION | DESCRIPTION |
|---|---|
| $E_1$ | benzophenone |
| $E_2$ | triphenyl phosphine oxide |
| $E_3$ | Permanax ™ WSP (antioxidant)* |
| $E_4$ | dilauryl thiodipropionate |
| $E_5$ | methyl formate |
| $E_6$ | ethyl formate |
| $E_7$ | methanol |
| $E_8$ | formaldehyde |
| $E_9$ | acetaldehyde |
| $E_{10}$ | acetone |

TABLE 3-continued

| ABBREVIATION | DESCRIPTION |
|---|---|
| $E_{11}$ | acrolein (2-propenal) |
| $E_{12}$ | propanal |

*$E_3$ = 2,2'-methylene bis (4-ethyl-6-(1-methylcyclohexyl)phenol).

TABLE 4

| EX. | $E_1$ | $E_2$ | $E_3$ | $E_4$ | $E_5$ | $E_6$ | $E_7$ | $E_8$ | $E_9$ | $E_{10}$ |
|---|---|---|---|---|---|---|---|---|---|---|
| 1 | 21 | 21 | <10 | <5 | <600 | <300 | 3,310 | 1,400 | 6,700 | 100 |
| COMP. 1 | <20 | 40 | <10 | <5 | <600 | <300 | 2,960 | 1,600 | 7,800 | 80 |

TABLE 5

| EX. | $E_1$ | $E_2$ | $E_3$ | $E_4$ | $E_5$ | $E_6$ | $E_7$ | $E_8$ | $E_9$ | $E_{10}$ |
|---|---|---|---|---|---|---|---|---|---|---|
| 1 | 22 | 13 | <10 | <5 | <600 | <300 | <600 | 320 | 780 | 50 |
| COMP. 1 | 21 | 16 | <10 | <5 | <600 | <300 | <600 | 310 | 730 | 50 |

In Table 6, two five-layer laminate structures in accordance with the invention, and one comparative four-layer laminate structure, are disclosed. The two five-layer structures were each made by laminating a coextruded four-layer film, using a conventional adhesive, to a second film (=layer 5). The comparative structure was made by laminating a coextruded three-layer film, using a conventional adhesive, to a second film (=layer 4).

TABLE 6

| EXAMPLE | STRUCTURE |
|---|---|
| 2 | $PE_2/ZB_2/OSB_2/EV_2//AD_2//F_1$ |
| 3 | $PE_2/ZB_3/OSB_2/EV_2//AD_2//F_1$ |
| COMP. 2 | $PE_2/OSB_2/EV_2//AD_2//F_1$ |

The target (and approximate actual) gauge (in mils) of each layer of the laminate structures of the invention was:

| layer 1 | layer 2 | layer 3 | layer 4 | adhesive | layer 5 |
|---|---|---|---|---|---|
| 0.20 | 0.20 | 0.50 | 1.00 | (minimal) | 0.50 |

The target (and approximate actual) gauge (in mils) of each layer of the comparative laminate structures was:

| layer 1 | layer 2 | layer 3 | adhesive | layer 4 |
|---|---|---|---|---|
| 0.40 | 0.51 | 1.04 | (minimal) | 0.50 |

The film of Examples 2 and 3 were subjected to food law migration tests to evaluate whether zeolites could remove oxidation by-products. Their efficacy was compared with Comparative 2. The list of extractables can be found in Table 3. The test results from the extraction of the films with Miglyol 812 (available from Hüls America), a fatty food simulant, are summarized in Table 7. Zeolites can reduce the concentration of certain extractables which could cause regulatory issues.

TABLE 7

| Migrant (ppb) | COMP. 2 | EX. 2 | EX. 3 |
|---|---|---|---|
| $E_9$ | <Q.L. | <Q.L. | <Q.L. |
| $E_{10}$ | <Q.L. | <Q.L. | <Q.L. |
| $E_{11}$ | <D.L. | <D.L. | <D.L. |
| $E_1$ | 980 | 1000 ± 5 | 875 ± 23 |
| $E_8$ | <D.L. | <D.L. | <D.L. |
| $E_{12}$ | <D.L. | <D.L. | <D.L. |

D.L. = detection limit = 50 parts per billion (food equivalent).
Q.L. = quantifiable limit = 150 parts per billion (food equivalent).

In Table 8, three five-layer laminate structures in accordance with the invention, and one comparative five-layer laminate structure, are disclosed. The five-layer structures were each made by laminating a coextruded four-layer film, using a conventional adhesive, to a second film (=layer 5).

TABLE 8

| EXAMPLE | STRUCTURE |
|---|---|
| 4 | $PE_2/ZB_2/OSB_3/EV_2//AD_2//F_1$ |
| 5 | $PE_2/ZB_3/OSB_3/EV_2//AD_2//F_1$ |
| 6 | $PE_2/ZB_4/OSB_3/EV_2//AD_2//F_1$ |
| COMP. 3 | $PE_2/PEB_2/OSB_3/EV_2//AD_2//F_1$ |

The target (and approximate actual) gauge (in mils) of each layer of the laminate structures of the invention and the comparative was:

| layer 1 | layer 2 | layer 3 | layer 4 | adhesive | layer 5 |
|---|---|---|---|---|---|
| 0.15 | 0.15 | 0.50 | 1.00 | (minimal) | 0.50 |

Sliced turkey breast was stored in packages made from the films of Examples 4, 5, 6 and Comparative 3. A sensory panel tasted the turkey slices to evaluate whether or not zeolites can reduce the off-flavor caused by byproducts of the oxygen-scavenging reaction.

The films were triggered by ultraviolet light according to the procedure disclosed in U.S. Pat. No 5,211,875. The films were converted into packages on a Multivac® R7000 packaging machine. Cryovac® T6070B film was used as the bottom web of the packages. Each package contained one slice of turkey. Each package was flushed with a gas mixture consisting of 99% $N_2$ and 1% $O_2$. Packages were stored in the dark for 7 days at 40° F.

A sensory panel rated the taste of the turkey slices. The scale ranged from 1 to 6, with 1 indicating extreme off-flavor and 6 indicating no off-flavor. The average scores are summarized in Table 9. In some cases, zeolites can reduce the off-flavor caused by the byproducts of the oxygen-scavenging reaction.

TABLE 9

| Film | Average Score |
|---|---|
| 4 | 2.3 |
| 5 | 3.9 |
| 6 | 2.5 |
| COMP. 3 | 2.6 |

In Table 10, two five-layer laminate structures in accordance with the invention, and two comparative five-layer laminate structure, are disclosed. The five-layer structures were each made by laminating a coextruded four-layer film, using a conventional adhesive, to a second film (=layer 5).

TABLE 10

| EXAMPLE | STRUCTURE |
|---|---|
| 7 | $ZB_5/PPB_1/OSB_4/ZB_6//AD_2//F_1$ |
| COMP. 4 | $PE_2/PPB_1/OSB_4/PE_2//AD_2//F_1$ |
| 8 | $ZB_5/PPB_2/OSB_4/ZB_6//AD_2//F_1$ |
| COMP. 5 | $PE_2/PPB_2/OSB_4/PE_2//AD_2//F_1$ |

The target (and approximate actual) gauge (in mils) of each layer of the laminate structures of the invention and the comparative was:

| layer 1 | layer 2 | layer 3 | layer 4 | adhesive | layer 5 |
|---|---|---|---|---|---|
| 0.15 | 0.15 | 0.50 | 1.00 | (minimal) | 0.50 |

Sliced turkey breast was stored in packages made from the films of Examples 7 and 8 and Comparatives 4 and 5. A sensory panel tasted the turkey slices to evaluate whether or not zeolites can reduce the off-flavor caused by the byproducts of the oxygen-scavenging reaction.

The films were triggered by ultraviolet light according to the procedure disclosed in U.S. Pat. No 5,211,875. The films were converted into packages on a Multivac® R7000 packaging machine. Cryovac® T6070B film was used as the bottom web of the packages. Each package contained one slice of turkey. Each package was flushed with a gas mixture consisting of 99% $N_2$ and 1% $O_2$. Packages were stored in the dark for 7 days at 40° F.

A sensory panel rated the taste of the turkey slices. The scale ranged from 1 to 6, with 1 indicating extreme off-flavor and 6 indicating no off-flavor. Table 11 summarizes the percentage of the panelists which did not taste an off-flavor (i.e. a score of 6) in the packaged turkey slices. In some cases, zeolites can significantly reduce the off-flavor caused by the byproducts of the oxygen-scavenging reaction.

TABLE 11

| Film | Percentage of Panelist which did not taste an off-flavor in the packaged turkey |
|---|---|
| 7 | 39% |
| COMP. 4 | 17% |
| 8 | 17% |
| COMP. 5 | 13% |

A headspace gas chromatography (GC) method was used to determine the ability of a material to absorb aldehydes. The material (either 6 to 7 mg of powder or 25 mm disk of LLDPE film containing 4% absorber) was placed in a headspace GC vial (22 mL), and 2 µL of an aldehyde mixture containing about 0.1% each of the indicated aldehydes in methanol was injected into each vial. The vials were incubated at 80° C. for 1 hour and were injected into a GC. The data in Table 12 shows the percent change in the aldehyde concentration for each material relative to an appropriate control (vial with no absorber or LLDPE disk).

TABLE 12

Percent of Aldehydes Absorbed by Candidate Absorbers

| Sample | Propenal | Pentanal | Hexanal | Heptanal | Octanal |
|---|---|---|---|---|---|
| Percent Change Relative to Aldehyde Control | | | | | |
| $Z_5$ | −77 | 4 | −18 | −21 | −28 |
| $Z_6$ | −57 | −93 | −99 | −100 | −100 |
| Percent Change Relative to LLDPE Control | | | | | |
| $Z_4$ | −95 | n/t[c] | −100 | −85 | n/t |
| $Z_3$ | −92 | n/t | −77 | −100 | n/t | n/t means not included in this test.

The data in Table 12 shows that various zeolites are capable of reducing the migration of aldehydes. In addition, due to specificity of various materials it can be seen that blends of materials can be advantageous.

Films of the invention can been made by any conventional means, including coextrusion, lamination, extrusion coating, or corona bonding, and then optionally irradiated and/or oriented. They can be made heat shrinkable through orientation or tenterframing if desired, at orientation ratios of 1:2 to 1:9 in either or both of the machine and transverse directions. For shrink applications, they can be made to have a free shrink of at least 10%, more preferably at least 20%, most preferably at least 30%, in either or both directions at 90° C.

Gasket compositions of the invention can be made by any conventional process, including, but not limited to, extrusion compounding for thermoplastic compositions, and conventional mixing equipment for plastisol compositions. The gasket compositions of the invention can then be formed into gaskets on lids by any conventional process, including but not limited to, cold molding processes, inserted discs, application of liquid plastisols via pressurized nozzles followed by solidification in an oven, etc.

Various changes and modifications may be made without departing from the scope of the invention defined below. For example, a blend of different zeolites can be used in the same article (e.g. film or sealing composition). In films, although it is preferred that the zeolite be used in the film and as a packaging material such that the zeolite is disposed closer to the contents of the package, which can be food or any oxygen-sensitive product, than the oxygen scavenger, there may be applications where the zeolite is disposed "outside of" the oxygen scavenger, such that the oxygen scavenger-containing layer is disposed closer to the contents of a package made from the film, than the zeolite-containing layer. The zeolite can alternatively be disposed on both sides of the oxygen scavenger. Also, within the same film, a first zeolite can be used in a first layer, and a second zeolite, different from the first zeolite, can be used in another layer of the film.

Alternatively, the zeolite, in addition to or instead of the arrangements described above, can be disposed in the same layer or layers as the oxygen scavenging material. Thus, by way of example, any of layers 14, 34, 44, and 54 of the examples and figures can include any suitable percent, by weight of the layer, of a zeolite. A preferred blend of oxygen scavenging and zeolite in such a blend layer is between 95% and 99.5% oxygen scavenger, and between 0.5% and 5% zeolite. Any suitable polymeric materials can be employed in films containing the zeolites, and are not limited to those listed herein.

The amount of zeolite used in a film of the present invention is preferably between 0.1% and 5% of the layer in which it occurs. These percentages are based on the zeolite material (e.g. zeolite) per se, with suitable adjustment to be made if the zeolite material is used as a masterbatch with another material such as polyethylene. Above 5% of the layer, optics of the film can be compromised to some extent, although the film can still be used in many applications. In end-use applications where optics are not a critical feature of the package, such as opaque films or gaskets for containers, higher amounts of zeolites can be beneficially used.

Zeolites disclosed herein can be used with or in films or coatings, or absorbed into a variety of other supports for scavenging or other uses, such as a layer or coating on another object, or as a bottle cap or bottle liner, as an adhesive or non-adhesive insert, sealant, gasket, fibrous matte or other inserts, or as a non-integral component of a rigid, semi-rigid, or flexible container.

What is claimed is:

1. A polymeric sealing composition comprising an oxygen scavenger, and a zeolite, wherein the oxygen scavenger comprises a material selected from the group consisting of:
    i) an oxidizable compound and a transition metal catalyst,
    ii) an ethylenically unsaturated hydrocarbon and a transition metal catalyst,
    iii) an ascorbate,
    iv) an isoascorbate,
    v) a sulfite,
    vi) an ascorbate and a trasition metal catalyst, the catalyst comprising a simple metal, salt, complex, chelate, or compound of the transition metal,
    vii) a transition metal complex or chelate of a polycarboxylic acid, salicylic acid, or polyamine,
    viii) a reduced form of a quinone, a photoreducible dye, or a carbonyl compound which has absorbence in the UV spectrum, and
    ix) a tannin.

2. The sealing composition of claim 1 wherein the sealing composition is in the form of a gasket.

3. The gasket of claim 2 wherein the gasket adheres a lid to a rigid or semi-rigid container.

4. A package comprising:
    a) an oxygen-sensitive article; and
    b) a container into which the oxygen sensitive article is disposed, the container including a polymeric sealing composition comprising an oxygen scavenger, and a zeolite, wherein the oxygen scavenger comprises a material selected from the group consisting of:
        i) an oxidizable compound and a transition metal catalyst,
        ii) an ethylenically unsaturated hydrocarbon and a transition metal catalyst,
        iii) an ascorbate,
        iv) an isoascorbate,
        v) a sulfite,
        vi) an ascorbate and a transition metal catalyst, the catalyst comprising a simple metal, salt, complex, chelate, or compound of the transition metal,
        vii) a transition metal complex or chelate of a polycarboxylic acid, salicylic acid, or polyamine,
        viii) a reduced form of a quinone, a photoreducible dye, or a carbonyl compound which has absorbence in the UV spectrum, and
        ix) a tannin.

5. The package of claim 4 wherein the oxygen scavenger comprises a material selected from the group consisting of:
    i) an ethylenically unsaturated hydrocarbon and a transition metal catalyst,
    ii) a transition metal complex or chelate of a polycarboxylic acid, salicylic acid, or polyamine, and
    iii) a reduced form of a quinone, a photoreducible dye, or a carbonyl compound which has absorbence in the UV spectrum.

6. The sealing composition of claim 1 wherein the oxygen scavenger comprises a material selected from the group consisting of:

i) an ethylenically unsaturated hydrocarbon and a transition metal catalyst, ii) a transition metal complex or chelate of a polycarboxylic acid, salicylic acid, or polyamine, and iii) a reduced form of a quinone, a photoreducible dye, or a carbonyl compound which has absorbence in the UV spectrum.

7. A method of making a polymeric sealing composition having reduced migration of by-products of an oxygen scavenging reaction comprising:

a) providing a polymeric sealing composition comprising an oxygen scavenger, and a zeolite, wherein the oxygen scavenger comprises a material selected from the group consisting of:

i) an oxidizable compound and a transition metal catalyst, ii) an ethylenically unsaturated hydrocarbon and a transition metal catalyst, iii) an ascorbate, iv) an isoascorbate, v) a sulfite, vi) an ascorbate and a transition metal catalyst, the catalyst comprising a simple metal, salt, complex, chelate, or compound of the transition metal, vii) a transition metal complex or chelate of a polycarboxylic acid, salicylic acid, or polyamine, viii) a reduced form of a quinone, a photoreducible dye, or a carbonyl compound which has absorbence in the UV spectrum, and ix) a tannin; and b) exposing the article to actinic radiation.

* * * * *